(12) United States Patent
Jones (10) Patent No.: US 10,765,887 B2
(45) Date of Patent: Sep. 8, 2020

(54) PHOTOTHERAPY DEVICE

(71) Applicant: Thera B Medical Products, Inc., East Lansing, MI (US)

(72) Inventor: Alexa Jones, Lansing, MI (US)

(73) Assignee: Thera B Medical Products, Inc., East Lansing, MI (US)

( * ) Notice: Subject to any disclaimer, the term of this patent is extended or adjusted under 35 U.S.C. 154(b) by 0 days.

(21) Appl. No.: 15/874,973

(22) Filed: Jan. 19, 2018

(65) Prior Publication Data
US 2018/0207446 A1    Jul. 26, 2018

Related U.S. Application Data

(60) Provisional application No. 62/448,461, filed on Jan. 20, 2017.

(51) Int. Cl.
*A61N 5/06* (2006.01)

(52) U.S. Cl.
CPC .... *A61N 5/0621* (2013.01); *A61N 2005/0645* (2013.01); *A61N 2005/0652* (2013.01); *A61N 2005/0654* (2013.01); *A61N 2005/0663* (2013.01)

(58) Field of Classification Search
CPC .................................................. A61N 5/0621
See application file for complete search history.

(56) References Cited

U.S. PATENT DOCUMENTS

| | | | | |
|---|---|---|---|---|
| 6,045,575 A | * | 4/2000 | Rosen | A61N 5/0621 2/905 |
| 6,596,016 B1 | * | 7/2003 | Vreman | A61N 5/0621 128/903 |
| 2004/0039428 A1 | * | 2/2004 | Williams | A61N 5/0621 607/91 |
| 2004/0138726 A1 | * | 7/2004 | Savage, Jr. | A61N 5/0621 607/88 |
| 2006/0089686 A1 | * | 4/2006 | Streibich | A61N 5/0621 607/88 |
| 2008/0116401 A1 | * | 5/2008 | Rice | A61N 5/0621 250/516.1 |
| 2009/0018622 A1 | * | 1/2009 | Asvadi | A61N 5/0621 607/91 |
| 2010/0179469 A1 | * | 7/2010 | Hammond | A61N 5/0603 604/20 |
| 2011/0301673 A1 | * | 12/2011 | Hoffer | A61N 5/0613 607/91 |
| 2012/0253433 A1 | * | 10/2012 | Rosen | A61N 5/0621 607/91 |
| 2013/0144364 A1 | * | 6/2013 | Wagenaar Cacciola | A61N 5/0613 607/90 |

* cited by examiner

*Primary Examiner* — John R Downey
(74) *Attorney, Agent, or Firm* — The Watson IP Group, PLC; Jovan N. Jovanovic (57) ABSTRACT

A phototherapy device comprising an outer garment wrap and a lamp assembly. The outer garment wrap has an inner surface. The lamp assembly has a base layer and a frame defining a plurality of inner chambers. A LED lamp assembly is positioned within each of the plurality of inner chambers. The lamp assembly is positioned on the inner surface of the outer garment wrap. A protective lamp envelope for receipt of the lamp assembly and attachment thereof to the outer garment wrap is likewise disclosed.

7 Claims, 9 Drawing Sheets

PHOTOTHERAPY DEVICE

CROSS-REFERENCE TO RELATED APPLICATION

This application claims priority from U.S. Prov. Pat. App. Ser. No. 62/448,461 filed Jan. 20, 2017, entitled "Phototherapy Device," the entire disclosure of which is hereby incorporated by reference in its entirety.

BACKGROUND OF THE DISCLOSURE

1. Field of the Disclosure

The disclosure relates in general to medical devices, and more particularly, to a phototherapy device that is intended to, but not limited to, the treatment of jaundice.

2. Background Art

Jaundice is a disease that affects 60% of newborns. The disease can cause mental retardation or death if not treated immediately after birth. A commonly known treatment for jaundice is blue light therapy, or phototherapy, that is administered immediately after or soon after birth. Of course, other wavelengths may be used as well. Examples of commonly used devices include Biliblanket and Bilisoft, both of which are produced by GE Healthcare. Though these treatments effectively cure jaundice, they can be unpleasant to the infant. Additionally, these devices do not allow for maternal-infant bonding during treatment due to their cumbersome configurations.

Additionally, the devices that are known have other drawbacks. For example, some of the devices include a stiff light pad that can only cover portions of the body of the infant, and that cannot follow the contours of the body well. Other devices do not allow for the infant to be swaddled, or to be held by a mother, father or other caretaker, instead, the infant must lay in an exposed manner away from caretakers.

SUMMARY OF THE DISCLOSURE

The disclosure is directed to a phototherapy device comprising an outer garment wrap and a lamp assembly. The outer garment wrap has an inner surface. The lamp assembly has a base layer and a frame defining a plurality of inner chambers. A LED lamp assembly is positioned within each of the plurality of inner chambers. The lamp assembly is positioned on the inner surface of the outer garment wrap. A protective lamp envelope for receipt of the lamp assembly and attachment thereof to the outer garment wrap is likewise disclosed. The lamp assembly has sufficient flexibility and cushioning to follow the contours of the infant more closely, and to provide enhanced comfort.

BRIEF DESCRIPTION OF THE DRAWINGS

The disclosure will now be described with reference to the drawings wherein.

DETAILED DESCRIPTION OF THE DISCLOSURE

While this disclosure is susceptible of embodiment in many different forms, there is shown in the drawings and described herein in detail a specific embodiment(s) with the understanding that the present disclosure is to be considered as an exemplification and is not intended to be limited to the embodiment(s) illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Figure 1:
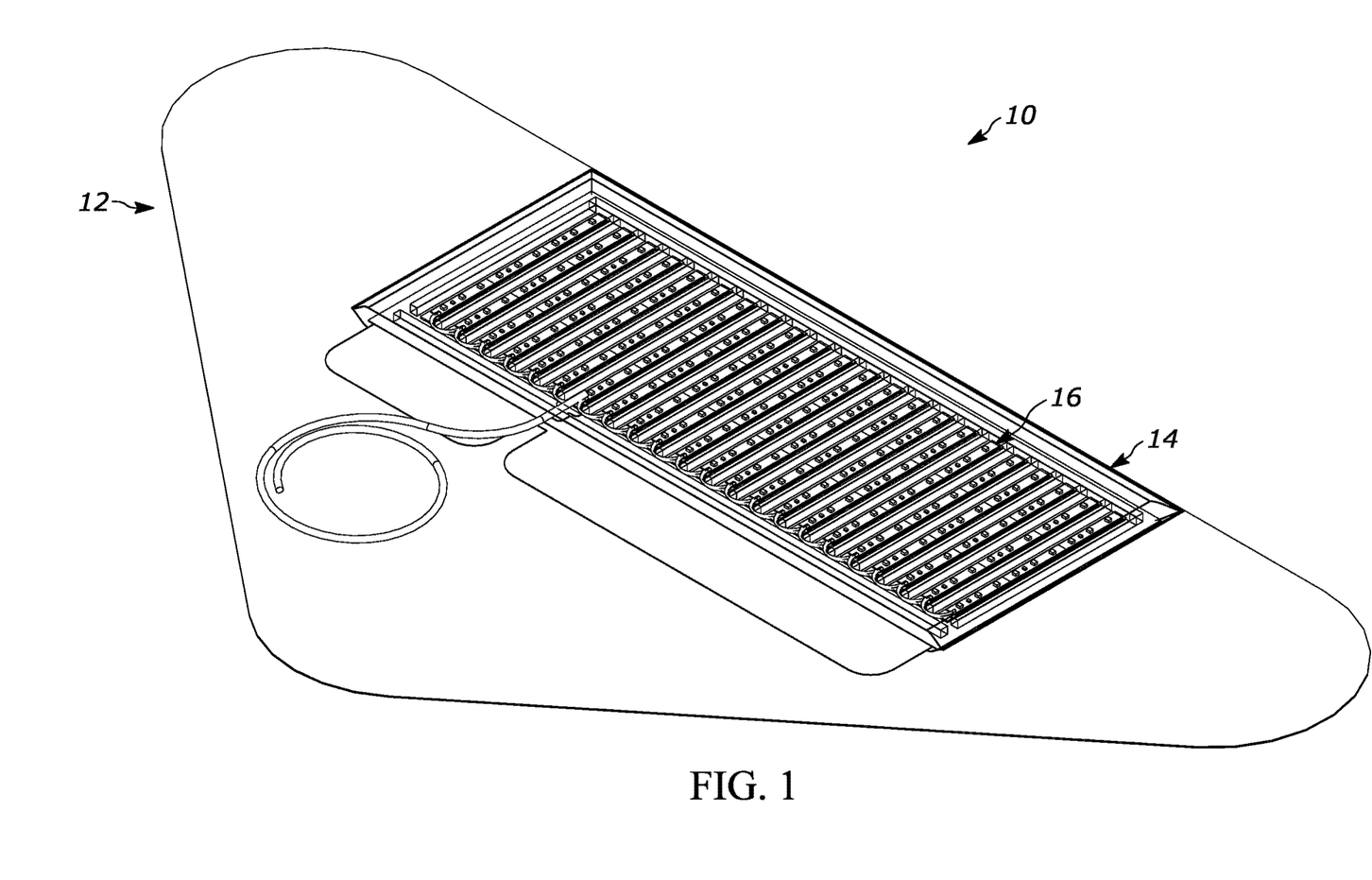
FIG. 1 of the drawings is a top perspective view of a configuration of the phototherapy device of the present disclosure.
Figure 2:
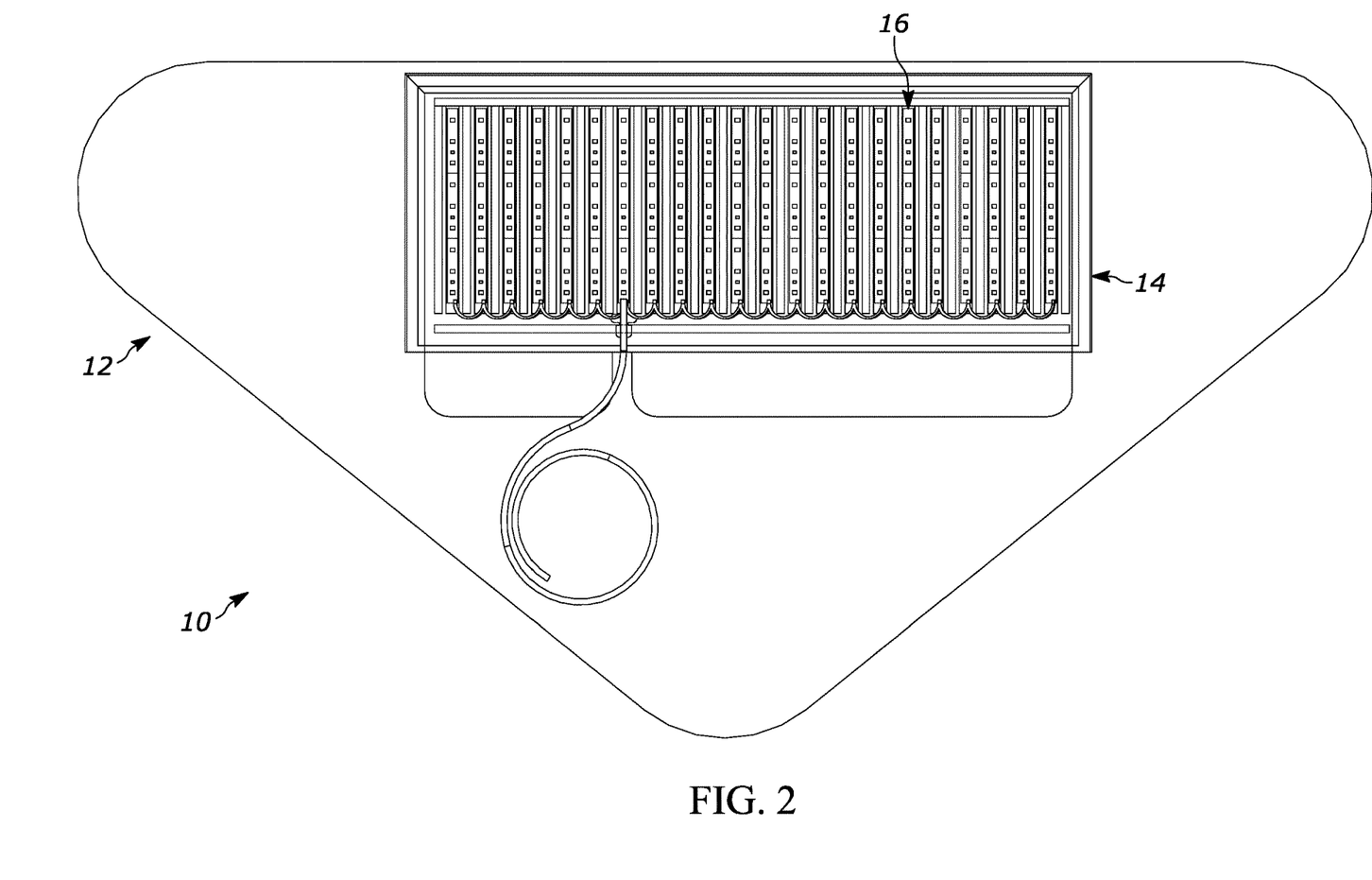
FIG. 2 of the drawings is a top plan view of a configuration of the phototherapy device of the present disclosure.

Referring now to the drawings and in particular to FIGS. 1 and 2, the disclosure is directed to a phototherapy device shown generally at 10. The phototherapy device is primarily suited for the treatment of jaundice in infants, but it is not strictly limited thereto. Of course, the configuration of the components lends itself to such use. It will be understood that such treatment generally involves the application of light of a particular range of wavelength (in the blue visible light range of the spectrum). The disclosure is not limited to a particular wavelength of light, and it is also contemplated that some wavelengths may be visible or not visible to the human eye.

Figure 3:
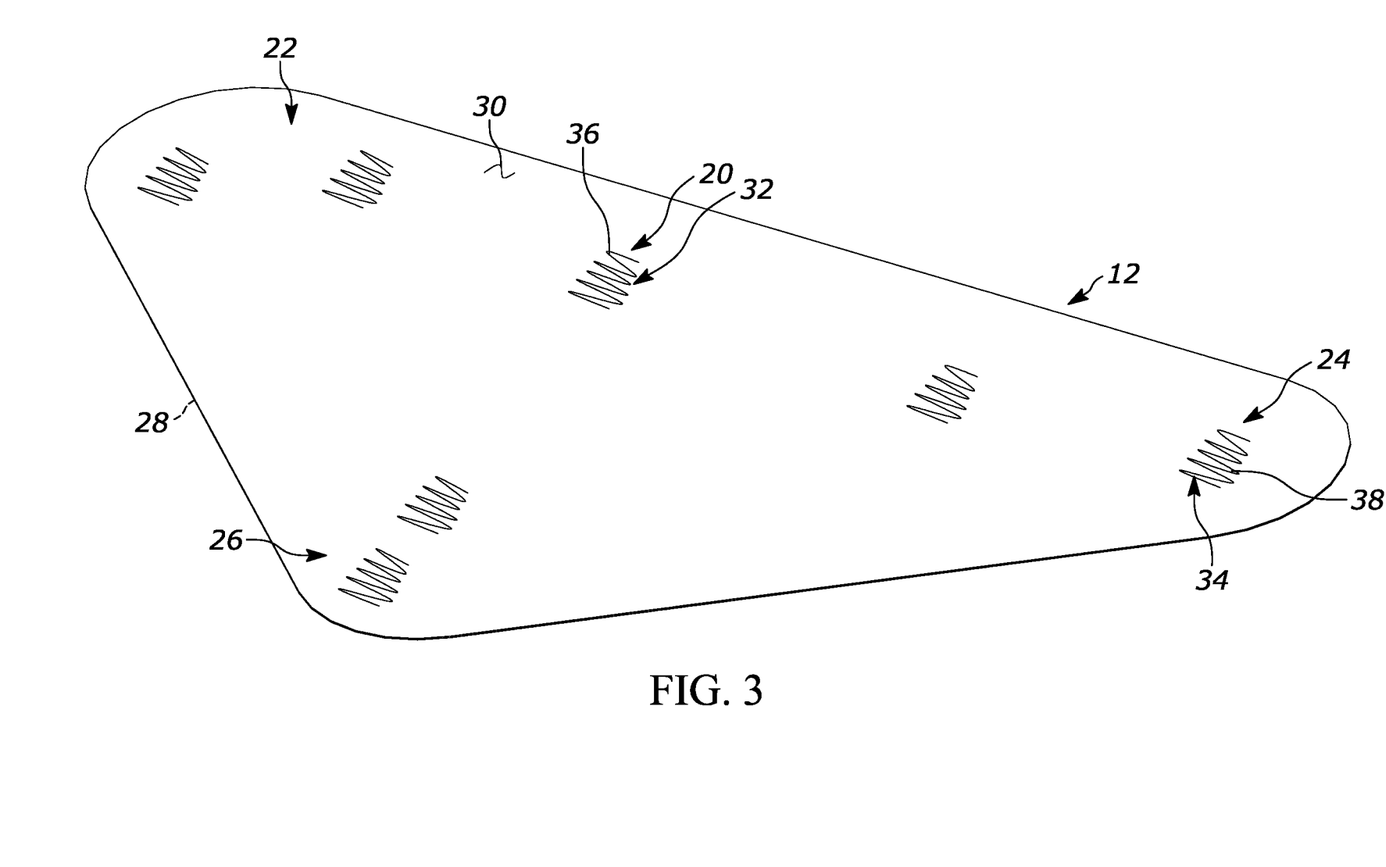
FIG. 3 of the drawings is a top perspective view of the outer garment wrap of the phototherapy device of the present disclosure.
Figure 4:
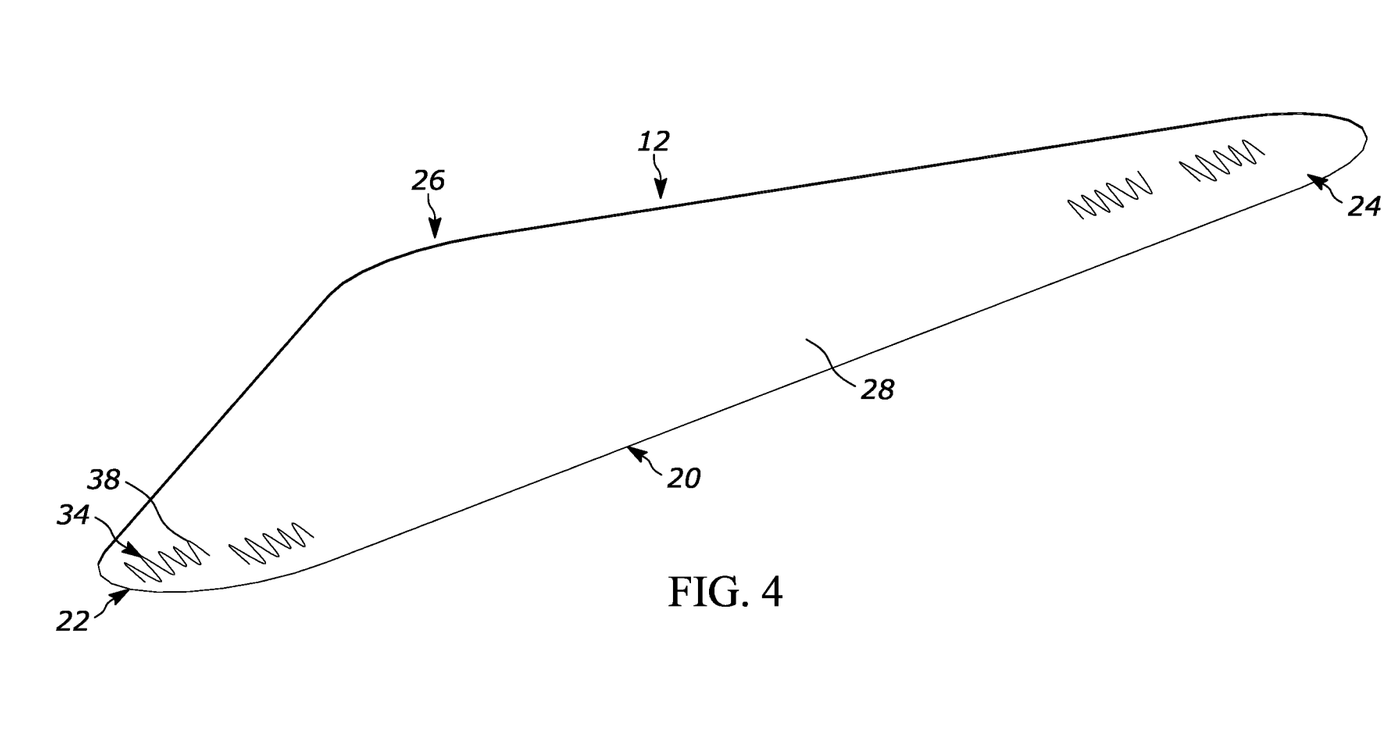
FIG. 4 of the drawings is a bottom perspective view of the outer garment wrap of the phototherapy device of the present disclosure.

In the configuration shown, and with reference to FIGS. 1 and 2, the phototherapy device 10 includes outer garment wrap 12, protective lamp envelope 14 and lamp assembly 16. With further reference to FIGS. 3 and 4, the outer garment wrap 12 comprises a woven or non-woven natural or synthetic fabric. In some configurations, it is contemplated that the outer garment wrap may comprise a swaddle or the like. The swaddle may be formed from flannel, muslin and/or gauze, among a number of different materials.

The outer garment wrap 12 includes central body portion 20, first wing 22, second wing 24 and lower extension 26. The outer garment wrap further defines an outer surface 28 and an inner surface 30. The inner surface generally comprises the infant contact surface and the surface to which the lamp is assembly is mounted. A number of different shapes and sizes are contemplated. It is, for example, contemplated that different sizes may be offered to accommodate differently sized infants, etc. And, the particular configuration of the outer garment wrap is not to be deemed limiting.

To facilitate the attachment of the protective lamp assembly and associated materials to the outer garment wrap, a plurality of light pad coupling members 32 may be provided. In the configuration shown, these light pad members may comprise any number of different structures, including, but not limited to, hook and loop fastener structures, such as hook and loop fastener structure 36. These are positioned and attached to the outer garment wrap on the inner surface thereof. It will also be understood that a plurality of garment wrap coupling members 34 may be disposed on the outer surface 28 and the inner surface 30 of the outer garment wrap so as to facilitate the swaddling of the garment wrap and to facilitate the maintenance of the garment wrap in the swaddled configuration. In other configurations, buttons, snaps, pins, adhesive, magnets and other structures may be utilized for each of the light pad coupling member and the garment wrap coupling members.

Figure 5:
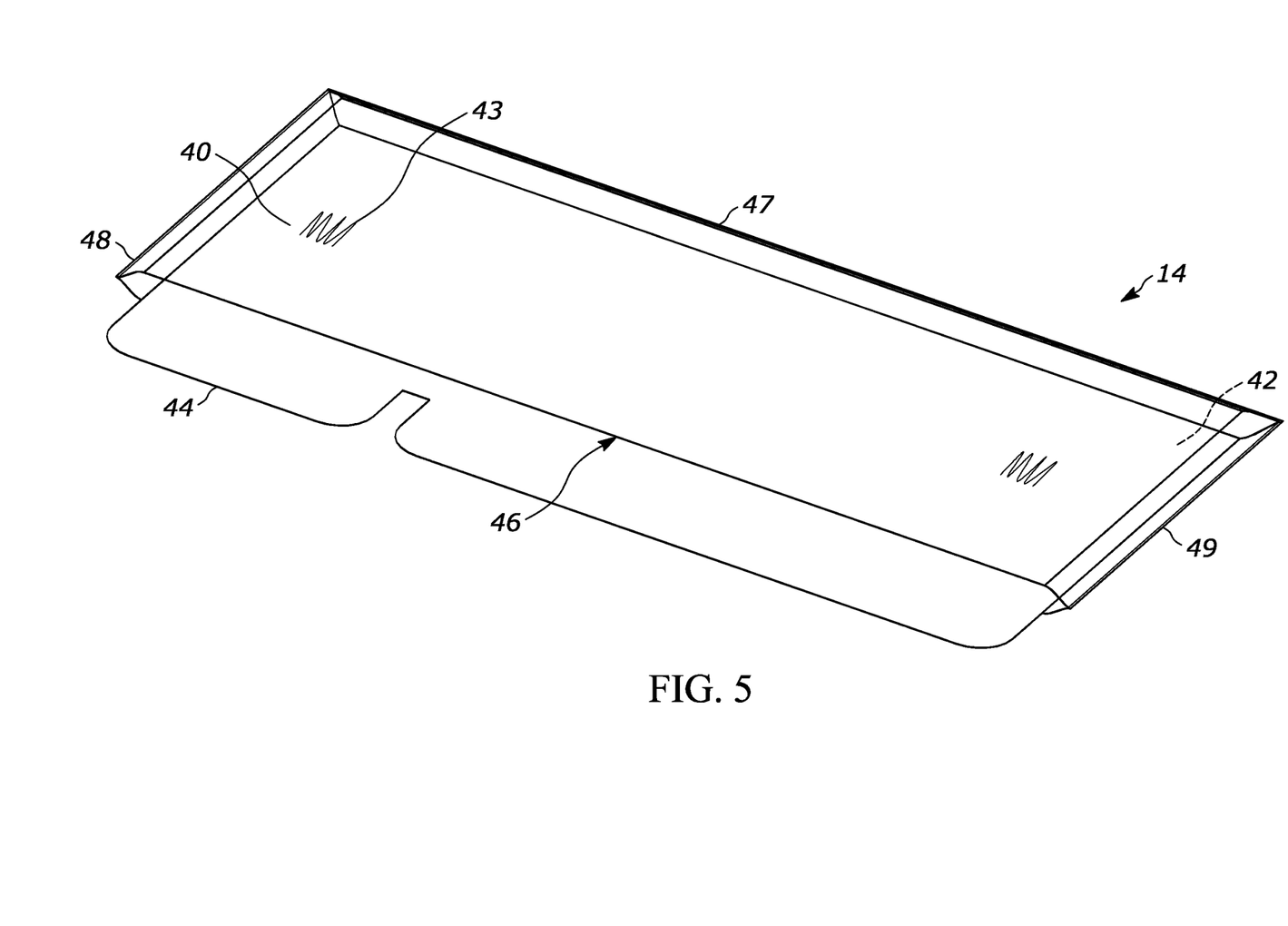
FIG. 5 of the drawings is a top perspective view of the protective lamp envelope of the phototherapy device of the present disclosure.

The protective lamp envelope is shown in more detail in FIG. 5 as comprising, preferably, a clear PVC or other partially or completely transparent or translucent polymer material (while it will be understood that certain portions may be opaque). The envelope formed from a front panel 40, a back panel 42 and a closure panel. It will be understood that the panels may be formed from three or more discrete pieces of material, or may be formed from a single piece of material that is folded over itself. The different panels are sealed together to form a bottom seal 47, a first side seal 48 and a second side seal 49, thereby leaving an open top with the closure panel being foldable thereover. In particular, the outer perimeter of the front and back panels are sealed about three sides to form the seals 47 through 49. It will be understood that at the side seals or the bottom seal, gussets may be formed so as to provide room for the envelope to expand, and to allow the front panel and the back panel to be pulled away from each other. The envelope further defines an inner cavity which is accessed through the top edges of the front and back panel, keeping in mind that the closure panel may be extended over the opening. In the configuration shown, the closure panel is integrally formed with the back panel and extends beyond the top of the front panel so that it can be folded over itself.

It will be understood that a closure mechanism may be provided on the closure panel, or the front panel, or both to maintain the closure panel in the desired configuration. For example, such a closure mechanism may comprise a hook and loop fastener system, an adhesive system, snaps, locking tabs and slots, among other structures. In other configurations, the flexibility of the material itself from which the envelope is formed may be sufficient in and of itself to maintain the closure panel in the desired configuration.

Additionally, the back panel may include a plurality of matching hook and loop fasteners 43 that are configured to engage the hook and loop fasteners of the light pad coupling members. In other configurations, other mating structures may be utilized (other than hook and loop fasteners. In still other configurations, the back panel may itself be formed from a material that is compatible with a hook and loop fastener material.

With reference to FIGS. 6 through 9, the lamp assembly 16 includes base layer 50, frame 52, lamp support 54, LED lamp assembly 56 and main power supply conductor 58. It will be understood that the lamp assembly can be entirely placed within the protective lamp envelope. The base layer 50 comprises a flexible material to which the frame 52 and the remaining components may be coupled. For example, one such material comprises a marine vinyl that is generally flexible but shape maintaining (that is, the material generally does not stretch). In other configurations, other materials having similar flexibility and general resistance to stretch may be utilized. The base layer includes upper surface 60 and lower surface 61. Generally, the material comprises a substantially uniform film of a predetermined thickness. One such marine vinyl is sold by Jo-Ann Fabrics under Part Number 4789087.

Figure 6:
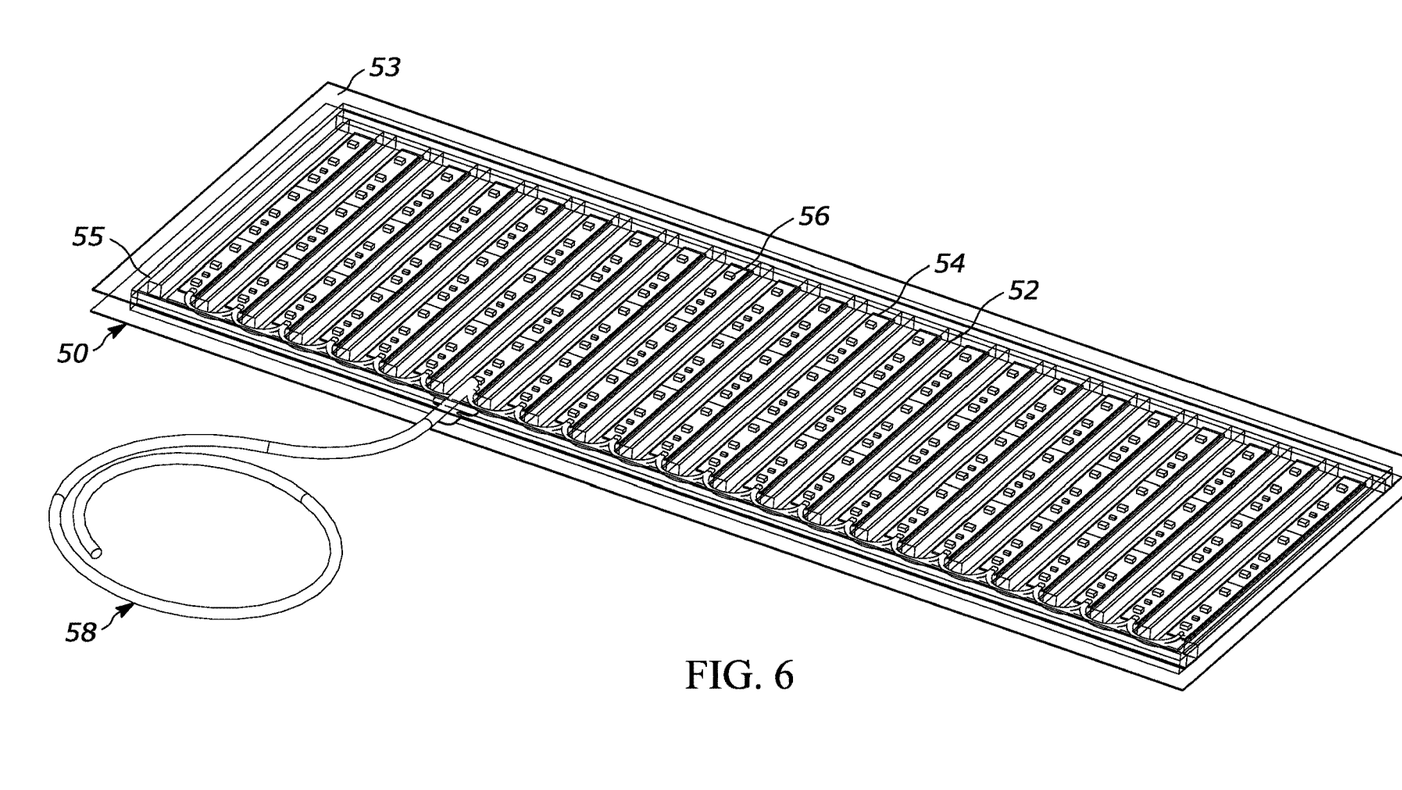
FIG. 6 of the drawings is a top perspective view of the lamp assembly of the phototherapy device of the present disclosure.
Figure 7:
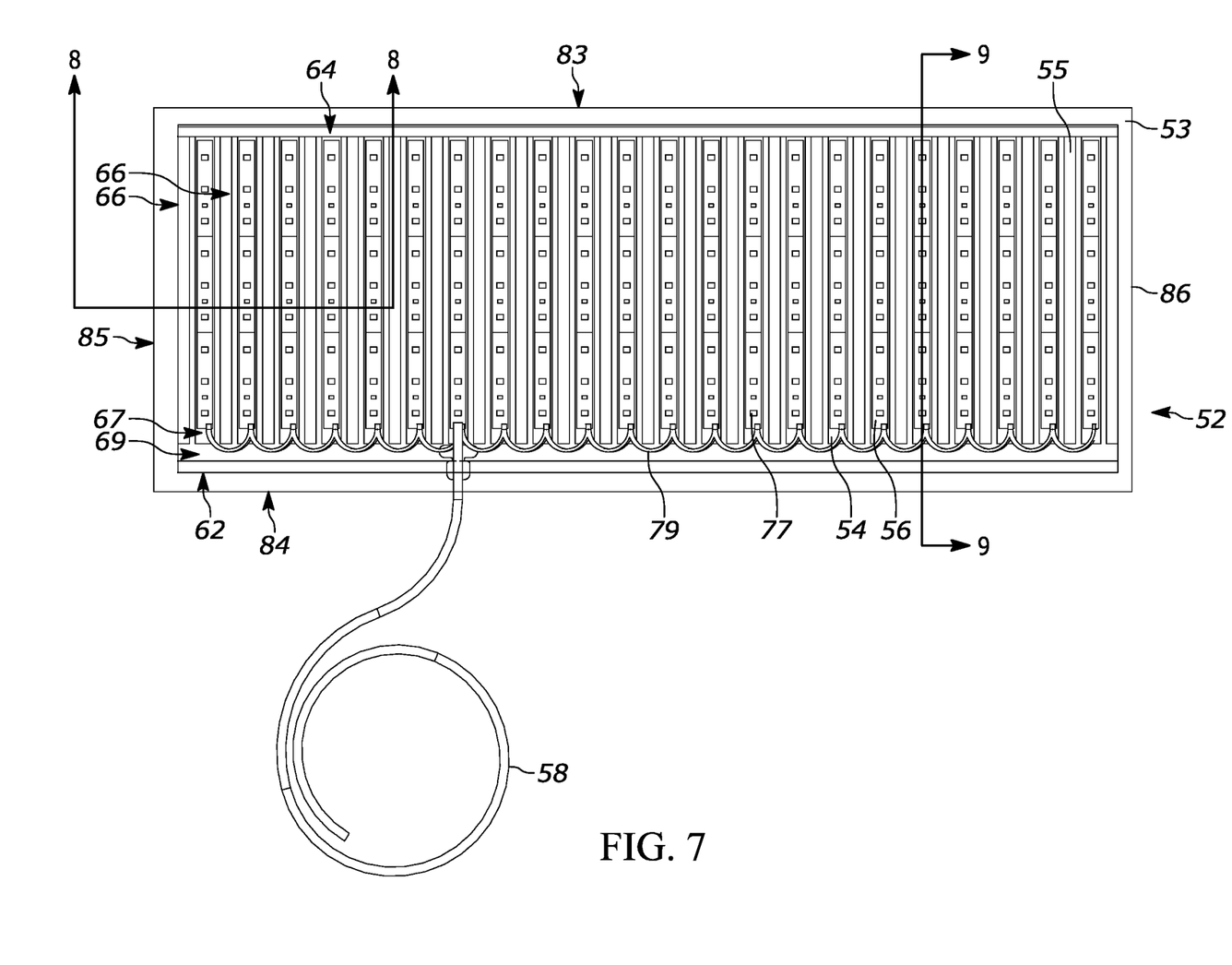
FIG. 7 of the drawings is a top plan view of the lamp assembly of the phototherapy device of the present disclosure.

In the configuration shown, the base layer comprises a generally rectangular member having longer sides 83, 84 and longer sides 85, 86. In other configurations other sizes and shapes are contemplated. For example, different shapes wherein the shape may be utilized to facilitate folding in a desired manner. In other configurations, the different shapes may be utilized to more closely follow the body contours of the infant when the outer garment wrap is swaddled about the infant.

The frame is defined by a top elongated member 62, a bottom elongated member 64 and a plurality of connector members 66. The top elongated member 62 extends along the longer side 85 (between the sides 83, 84), and generally parallel thereto. The bottom elongated member 64 extends along the longer side 86 (between the sides 85, 86), and generally parallel thereto, and parallel to the top elongated member 62 in a spaced apart orientation. The connector members 66 extend from the bottom elongated member 64, generally perpendicular thereto, toward the top elongated member, stopping just short thereof, preferably, or otherwise leaving a space between the connector member and the top elongated member. The connector members are spaced apart from each other a predetermined distance and generally parallel to each other, so as to define a plurality of inner chambers 67 and a top elongated channel 69 that extends between the upper end of the connector members and the top elongated member.

Figure 8:
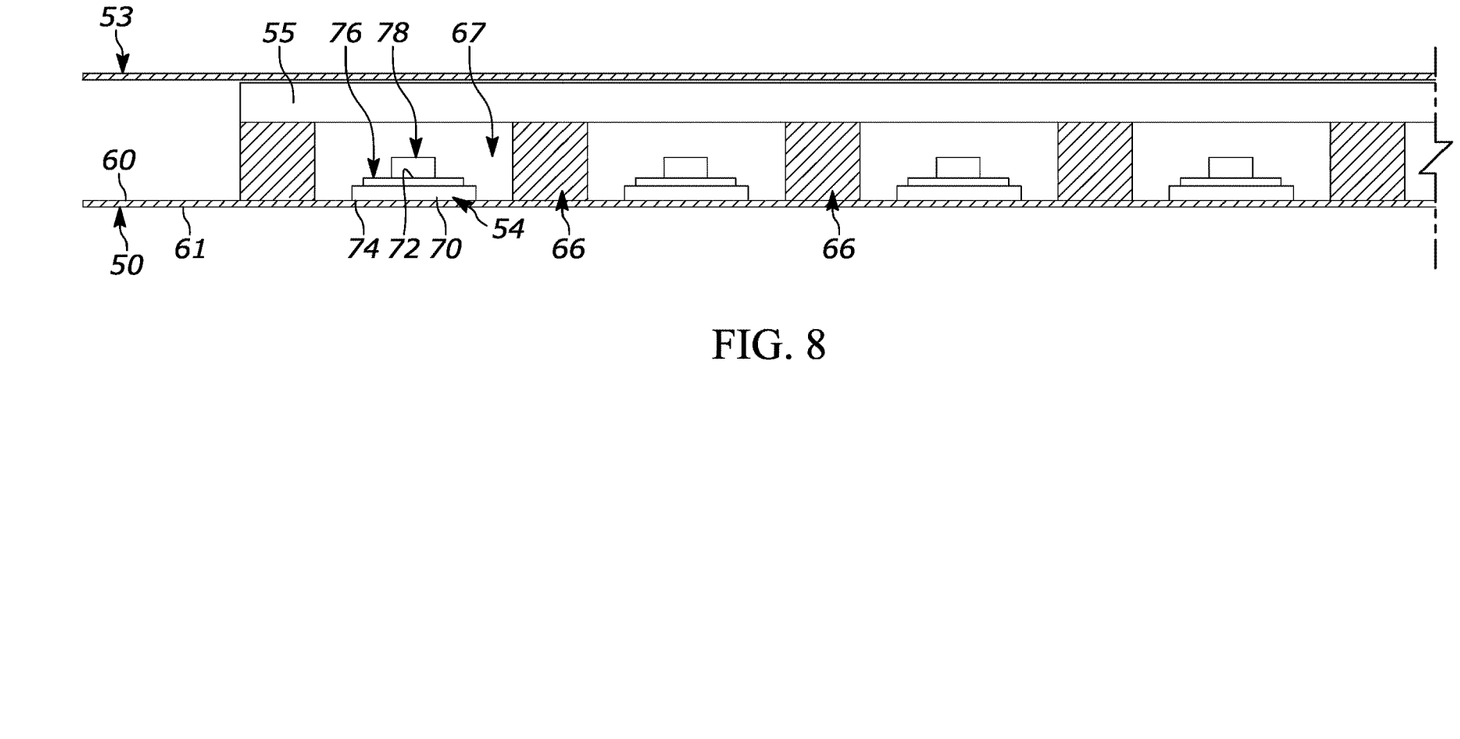
FIG. 8 of the drawings is a partial cross-sectional view of the lamp assembly of the phototherapy device of the present disclosure, taken generally about lines 8-8 of FIG. 7.
Figure 9:
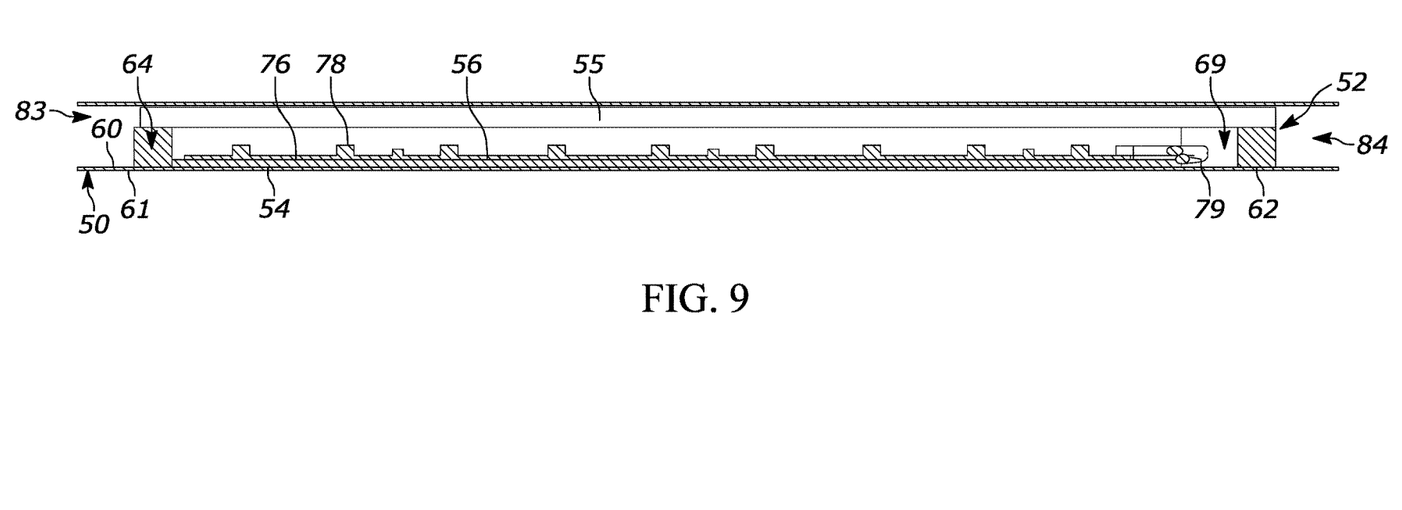
FIG. 9 of the drawings is a cross-sectional view of the lamp assembly of the phototherapy device of the present disclosure, taken generally about lines 9-9 of FIG. 7.

In the configuration shown, these members comprise a foam material that has a substantially square or rectangular cross-sectional configuration. In the configuration shown, the foam material has a square cross-sectional configuration with each leg of the square being 0.25 inches. In other configurations, materials of different configurations and shapes may be utilized. It is desirable to use a foam material that has an ability to compress and give when the infant is swaddled, so as to conform to the body, protecting the body from the LED lamp assembly and protecting the LED lamp assembly from crushing forces. The height of the foam above the base layer is such that it is greater than the height of the LED lamp assembly installed between the connector members. One such foam is offered by The Foam Factory under the part number VA2-250.

A translucent fabric or foam 55 may be positioned over the frame structure so as to obstruct direct vision of the different components of the lamp assembly, and to provide additional cushioning. For example, a fiber based material, or a foam material, may be utilized in such a case. As this is generally aesthetic, and cushion providing, it is contemplated that in other configurations, such a cover may be omitted, or made from a different material (and may include a design or the like).

A top layer 53 may be positioned above the frame and may have dimensions corresponding to the base layer so as to sandwich the frame and the LED lamp assembly therebetween. In such a configuration, the LED lamp assembly is protected from either side by the base layer and the top layer.

A lamp support 54 is positioned between adjacent connector members within the inner chambers so as to improve the rigidity of the base layer therebelow. In the configuration shown, the lamp support 54 comprises a plurality of stiffening pads that extend between the bottom elongated member and the top elongated member and between the adjacent connector members. In the configuration shown, the lamp support generally comprises a rectangular member formed from a nylon stiffening material having a thickness of 3/64" of an inch. Such a material provides the necessary rigidity to a localized area of the lamp assembly, upon which the LED lamp assemblies are coupled. As such, the base layer is allowed to flex and to be rolled up in a direction along the longer sides of the base layer, while the lamp support can preclude damage to the LED lamp assemblies during such an operation. The stiffening pad includes a top surface 72 and a bottom surface 74. The bottom surface is adjacent the upper surface 60 of the base layer, and overlies the same. The top surface is configured to receive the LED lamp assembly.

More specifically, the LED lamp assembly 56 includes a circuit board base 76 material which includes any necessary circuitry and a plurality of LED elements, such as LED element 78, mounted thereon. Generally, the base material is relatively rigid, as compared to the base layer, and, preferably, the lamp support. The base material 76 is attached to the top surface 72 of the stiffening pad. The LED elements 78 are positioned so as to direct light away from the board base 76. In the configuration shown, each LED lamp assembly includes a plurality of segments that are fashioned together end to end to stretch across each inner chamber. The LED lamp assembly 56 includes conductor leads 79 that extend from one end thereof proximate the top elongated channel 69. The conductor leads 79 are coupled to each other so as to place the different LED lamp assemblies in one of series and parallel electrical communication.

The main power supply conductor 58 is centrally located and attached to the conductor leads 79 at an inner end, with the outer end extending away from the base so that the outer end can be coupled to a battery pack (not shown), which is of a suitable size that it can be coupled to the outer surface 28 of the outer garment wrap. In such a manner, the entire phototherapy device 10 is completely self-sufficient and self-contained. That is, the infant can be carried and moved without fear that power will be cut off from the LED lamp assemblies. This is because the power supply and the LED lamp assemblies travel together, both being coupled to the infant.

It will be understood that, in the configuration shown, the main power supply conductor 58 is centrally positioned between the shorter sides 85, 86 and traverses across the top elongated member 62 so as to meet and be coupled to the conductor leads 79 at or near the top elongated channel 69.

To assemble the phototherapy device, the user first grasps the lamp assembly 16 and directs the lamp assembly into the protective lamp envelope 14, with the upper surface facing upwardly and adjacent the front panel 40 of the protective lamp envelope 14. The main power supply conductor 59 is directed out of the protective lamp envelope 14 and the closure panel 44 is folded over the front panel 40 to effectively close the envelop with the lamp assembly therein. The user may couple a power supply at this point, or a power supply may be integrated with the main power supply conductor.

Once positioned within the protective lamp envelope, the protective lamp envelope may be attached, via the fasteners 43 and the light pad coupling members 32. As the envelope is attached, the user can move the envelope relative to the outer garment wrap so as to achieve the desired position. Once positioned and coupled, the device is ready for use.

In particular, and as is shown in the Pictures attached as Additional Disclosure and made a part hereof, the infant is positioned, generally face up on the inner surface of the outer garment wrap. In such a position, the first and second wings are on either side of the infant, with the lower extension corresponding to the legs and/or feet of the infant. The infant is positioned on the protective lamp envelope as well. As the infant's weight presses against the envelope, the frame and the base layer can compress and flex to accommodate the infant without hurting or being uncomfortable to the infant. Next, the first and second wings are inwardly positioned so as to overlap. Once fully positioned, the user can wrap the lower extension upwardly so as to overlay a portion of the body of the infant and to complete and form the swaddle configuration. Of course other swaddles configurations can be utilized instead, wherein other patterns of wrapping are contemplated.

As the first and second wings are inwardly rotated into position, the protective lamp envelope and the lamp assembly are rotated inwardly. Again, due to the flexibility of the base layer and the frame, and the compression of the frame, the lamp assembly is capable of following the contours of the infant closely. Advantageously, the flexibility and compression capabilities allow for the LED lamp assembly to be positioned close to the skin of the infant while permitting an increased density of LED elements that can be utilized. While the structure is maintained, the ability to move with the infant and to adjust to differently sized infants provides a comfortable, wearable device in which infant discomfort is minimized.

It will further be understood that where the power source can be attached to the outer garment wrap (or integrated with the lamp assembly), the entire device and be fully self-contained. In such an instance, a user can carry the infant, and accomplish desired tasks with the infant (significantly, have maternal-infant bonding time), without being tied down to a stationary power supply and a long cord, or to a wall plug.

The foregoing description merely explains and illustrates the disclosure and the disclosure is not limited thereto except insofar as the appended claims are so limited, as those skilled in the art who have the disclosure before them will be able to make modifications without departing from the scope of the disclosure.

What is claimed is:

1. A phototherapy device comprising:
    an outer garment wrap, of the phototherapy device, having an inner surface and an outer surface; and
    a lamp assembly, of the phototherapy device, having a base layer and a frame positioned on the base layer, the frame comprising:
        a top elongated member, and a bottom elongated member spaced apart from each other, with a plurality of connector members extending therebetween and being substantially perpendicular to each of the top and bottom elongated members, each of connector members having an upper end, with the upper end being spaced apart from the top elongated member, to form a channel therebetween, the elongated members defining a plurality of inner chambers that are generally elongated and spaced apart from each other, with the top elongated member, the bottom elongated member and the connector members being formed from a foam material
    with a LED lamp assembly positioned within each of the plurality of inner chambers, and the LED lamp assemblies being electrically coupled together through connector leads that extend into the channel formed between the connector members and the top elongated member, wherein the lamp assembly is positioned within a protective lamp envelope that is detachably coupled to the inner surface of the outer garment wrap, the inner surface comprising an infant contact surface of the outer garment wrap.

2. The phototherapy device according to claim 1, further comprising a plurality of garment coupling members on the inner surface of the outer garment wrap, the plurality of garment coupling members coupling the outer garment wrap to the lamp assembly.

3. The phototherapy device according to claim 2, wherein the plurality of garment coupling members include at least one of a hook and loop fastener, buttons, snaps, pins, and magnets.

4. The phototherapy device according to claim 1, wherein the outer garment wrap includes a first wing, a second wing, and a lower extension that corresponds to legs or feet of an infant.

5. The phototherapy device according to claim 1, wherein the protective lamp envelope includes a translucent fabric or foam disposed against the lamp assembly.

6. The phototherapy device according to claim 1, wherein the protective lamp envelope includes a base layer disposed against the lamp assembly.

7. The phototherapy device according to claim 6, wherein the base layer is a marine vinyl.

\* \* \* \* \*